United States Patent
Hidaka et al.

(10) Patent No.: US 12,077,636 B2
(45) Date of Patent: Sep. 3, 2024

(54) HIGHLY SOLUBLE TRIS-(2,3-EPOXYPROPYL)-ISOCYANURATE AND METHOD FOR PRODUCING SAME

(71) Applicant: NISSAN CHEMICAL CORPORATION, Tokyo (JP)

(72) Inventors: Motohiko Hidaka, Tokyo (JP); Takashi Oda, Funabashi (JP); Nobuyuki Kakiuchi, Funabashi (JP); Hiroki Yamaguchi, Funabashi (JP)

(73) Assignee: NISSAN CHEMICAL CORPORATION, Tokyo (JP)

( * ) Notice: Subject to any disclaimer, the term of this patent is extended or adjusted under 35 U.S.C. 154(b) by 0 days.

(21) Appl. No.: 18/142,625

(22) Filed: May 3, 2023

(65) Prior Publication Data
US 2023/0287179 A1    Sep. 14, 2023

Related U.S. Application Data

(62) Division of application No. 16/402,305, filed on May 3, 2019, which is a division of application No. 14/759,486, filed as application No. PCT/JP2014/050063 on Jan. 7, 2014, now abandoned.

(30) Foreign Application Priority Data

Jan. 11, 2013 (JP) ................................. 2013-003377

(51) Int. Cl.
| | |
|---|---|
| C08G 73/06 | (2006.01) |
| C07D 405/14 | (2006.01) |
| C08G 59/32 | (2006.01) |
| C08G 59/42 | (2006.01) |
| C08G 59/68 | (2006.01) |
| C09D 179/04 | (2006.01) |
| C09J 179/04 | (2006.01) |

(52) U.S. Cl.
CPC ....... *C08G 73/0644* (2013.01); *C07D 405/14* (2013.01); *C08G 59/3245* (2013.01); *C08G 59/4215* (2013.01); *C08G 59/688* (2013.01); *C09D 179/04* (2013.01); *C09J 179/04* (2013.01); *Y10T 428/2982* (2015.01)

(58) Field of Classification Search
None
See application file for complete search history.

(56) References Cited

U.S. PATENT DOCUMENTS

| | | |
|---|---|---|
| 3,793,321 A | 2/1974 | Habermeier et al. |
| 6,124,381 A | 9/2000 | Miyake et al. |
| 6,903,212 B2 | 6/2005 | Ikeda et al. |
| 2012/0295199 A1 | 11/2012 | Takeyama et al. |

FOREIGN PATENT DOCUMENTS

| | | |
|---|---|---|
| CN | 102712741 A | 10/2012 |
| JP | H04-264123 A | 9/1992 |
| JP | H06-192396 A | 7/1994 |
| JP | H09-59352 A | 3/1997 |
| JP | 2000-007672 A | 1/2000 |
| JP | 2013-003377 A | 1/2013 |

OTHER PUBLICATIONS

Jul. 6, 2023 Office Action issued in U.S. Appl. No. 16/402,305.
Jul. 25, 2023 Office Action issued in Korean Patent Application No. 10-2022-7040732.
Vargha, Viktoria, Binary Solid-liquid Phase Diagram of the Two Diastereomer Racemates of Triglycidyl Isocyanurate (TGIC), European Polymer Journal, vol. 43, (2007), pp. 4762-4769.
Nakagi, Juji et al., "Thermal Behavior and Chemical Reactivities with Curing Agents of Stereoisomeric 1,3,5-Triglycidyl-s-triazinetrione," Japanese Journal of Plymer Science and Technology, vol. 47, No. 3, (1990), pp. 169-175.
Vargha, Viktoria et al., "Triglycidyl Isocyanurate Isomers," Die Angewandte Makromolekulare Chemie, vol. 228, (1995), pp. 25-40.
Endo, Yuki et al., "Triazine Kokkakuo Yusuru Shinki Ekijo Epoxy Jushi TEPIC-VL no Kokabutsu Bussei," Dai 62 Kai Network Polymer Koen Toronkai Koen Yoshishu, Oct. 12, 2011, pp. 135.
Takeyama, Toshiaki et al., "Shinki Tomei Ekijo Epoxy Jushi TEPIC-PAS," Dai 16 Material Yokoshu, (2007), pp. 198.
Apr. 8, 2014 Written Opinion issued in International Patent Application No. PCT/JP2014/050063.
Apr. 8, 2014 Search Report issued in International Patent Application No. PCT/JP2014/050063.
Endo et al., "Triazine Kokkahuo Yusuru Shinki Ekijo Epoxy Jushi TEPIC-VL no Kokabutsu Bussei," Dai 61 Kai Network Polymer Koen Toronkai Koen Yoshishu, Oct. 12, 2011, pp. 135.
Mar. 14, 2024 Office Action issued in U.S. Appl. No. 16/402,305.
Jun. 24, 2024 Notice of Allowance issued in U.S. Appl. No. 16/402,305.

*Primary Examiner* — Megan McCulley
(74) *Attorney, Agent, or Firm* — Oliff PLC

(57) ABSTRACT

There is provided an epoxy composition which has difficulty in precipitating a crystal during storage, is homogeneous and can be stored for a long period; and a cured product of the composition having excellent transparency, heat resistance, and light resistance can be obtained on curing. An α-type tris-(2,3-epoxypropyl)-isocyanurate crystal including β-type tris-(2,3-epoxypropyl)-isocyanurate in the crystal in a ratio of 2% by mass to 15% by mass. A method for producing the α-type tris-(2,3-epoxypropyl)-isocyanurate crystal including step (i) separating β-type tris-(2,3-epoxypropyl)-isocyanurate contained in a tris-(2,3-epoxypropyl)-isocyanurate solution from the solution as a solid to obtain a crystal with an increased content ratio of α-type tris-(2,3-epoxypropyl)-isocyanurate.

7 Claims, No Drawings

HIGHLY SOLUBLE TRIS-(2,3-EPOXYPROPYL)-ISOCYANURATE AND METHOD FOR PRODUCING SAME

This application is a divisional of application Ser. No. 16/402,305 filed May 3, 2019, which in turn is a divisional of application Ser. No. 14/759,486 filed Jul. 7, 2015, now abandoned, which in turn is a U.S. National Stage Entry of PCT/JP2014/050063 filed on Jan. 7, 2014, which in turn claims the benefit of Japanese Patent Application No. 2013-003377 filed Jan. 11, 2013. The entire disclosure of each of the prior applications is hereby incorporated by reference herein in its entirety.

TECHNICAL FIELD

The present invention relates to an α-type tris-(2,3-epoxypropyl)-isocyanurate crystal and a method for producing the same. Use of this crystal provides a composition having excellent solubility when a liquid composition is formed and difficulty in precipitating a crystal during long term storage, and provides a cured product having excellent transparency, high heat resistance, and high light resistance when the composition is cured by heating.

These compositions provide a transparent coating film which is applicable to a protection film and the like. A transparent composite sheet and a transparent composite film can be obtained by bonding transparent substrates. A glass cloth-reinforced transparent substrate can be obtained by curing a glass cloth in combination with the composition whose refractive index is matched with the refractive index of the glass cloth. This glass cloth-reinforced transparent substrate can be used as a lightweight substrate for replacing glass.

BACKGROUND ART

It has been known that tris-(2,3-epoxypropyl)-isocyanurate can provide a cured product having excellent transparency, heat resistance, and light resistance by curing tris-(2,3-epoxypropyl)-isocyanurate with a curing agent such as a carboxylic acid anhydride.

However, common tris-(2,3-epoxypropyl)-isocyanurate contains 25% by mass of β-type tris-(2,3-epoxypropyl)-isocyanurate and 75% by mass of α-type tris-(2,3-epoxypropyl)-isocyanurate. β-type is a crystal having a high melting point of about 150° C. and significantly low solubility. Consequently, when a homogenous composition dissolved with a solvent is intended to be formed from a curable composition containing the common tris-(2,3-epoxypropyl)-isocyanurate and a liquid carboxylic acid anhydride, the tris-(2,3-epoxypropyl)-isocyanurate is not dissolved. Even when the common tris-(2,3-epoxypropyl)-isocyanurate is dissolved, crystal is precipitated over time. Therefore, only limited liquid carboxylic acid anhydrides can be used and the curable composition cannot be stored. Consequently, the applicable range of tris-(2,3-epoxypropyl)-isocyanurate has been limited.

The α-type and β-type tris-(2,3-epoxypropyl)-isocyanurate have been disclosed as follows.

Tris-(2,3-epoxypropyl)-isocyanurate has three asymmetric carbons. A crystal formed of an equimolar mixture of (2R, 2′R, 2″R)-tris-(2,3-epoxypropyl)-isocyanurate and (2S, 2′S, 2″S)-tris-(2,3-epoxypropyl)-isocyanurate, in which the three asymmetric carbons have the same chirality, is generally called a 1-type crystal. It has been known that the 1-type crystal is a crystal having a high melting point of about 150° C. This is because these two enantiomers in a pair form a molecule lattice having strong 6 hydrogen bonds each other and thus forms a crystal lattice. The 1-type tris-(2,3-epoxypropyl)-isocyanurate crystal not only has the high melting point but also has significantly low solubility to various solvents. This 1-type tris-(2,3-epoxypropyl)-isocyanurate and the method for producing the same are disclosed (refer to Patent Document 1).

On the contrary, a crystal formed of a mixture of (2R, 2R, 2S)-tris-(2,3-epoxypropyl)-isocyanurate and (2S, 2S, 2R)-tris-(2,3-epoxypropyl)-isocyanurate, in which only one of the three asymmetric carbons has different optical anisotropy, is generally called an α-type crystal. The α-type crystal has different crystal structure from the β-type crystal described above and thus has a low melting point of about 100° C. This α-type tris-(2,3-epoxypropyl)-isocyanurate and the method for producing the same are also disclosed (refer to Patent Document 2).

PRIOR ART DOCUMENTS

Patent Documents

Patent Document 1: Japanese Patent Application Publication No. 2000-007672 (JP 2000-007672 A)
Patent Document 2: Japanese Patent Application Publication No. H4-264123 (JP H4-264123 A)

SUMMARY OF THE INVENTION

Problem to be Solved by the Invention

The purpose of the present invention is to provide tris-(2,3-epoxypropyl)-isocyanurate having excellent workability including high solubility during use and difficulty in precipitating a crystal during storage with maintaining excellent properties of tris-(2,3-epoxypropyl)-isocyanurate, that is, an α-type tris-(2,3-epoxypropyl)-isocyanurate crystal containing β-type tris-(2,3-epoxypropyl)-isocyanurate in a ratio of 2% by weight to 15% by weight. Use of this crystal can provide a composition that is homogeneous and can be stored for a long period. The cured product of the composition having excellent transparency, heat resistance, and light resistance can be obtained when the composition is cured.

Means for Solving the Problem

The present invention provides as a first aspect, an α-type tris-(2,3-epoxypropyl)-isocyanurate crystal containing β-type tris-(2,3-epoxypropyl)-isocyanurate in the crystal in a ratio of 2% by mass to 15% by mass;
  as a second aspect, the α-type tris-(2,3-epoxypropyl)-isocyanurate crystal according to the first aspect, in which β-type tris-(2,3-epoxypropyl)-isocyanurate is contained in the crystal in a ratio of 2% by mass to 10% by mass;
  as a third aspect, the α-type tris-(2,3-epoxypropyl)-isocyanurate crystal according to the first aspect or the second aspect, in which the crystal has a particle diameter of 1 μm to 500 μm;
  as a fourth aspect, a method for producing the α-type tris-(2,3-epoxypropyl)-isocyanurate crystal according to any one of the first aspect to the third aspect, the method comprising: (i) separating β-type tris-(2,3-epoxypropyl)-isocyanurate contained in a tris-(2,3-epoxypropyl)-isocyanurate solution from the solution as a solid to obtain a crystal with an increased content ratio of α-type tris-(2,3-epoxypropyl)-isocyanurate;

as a fifth aspect, a method for producing the α-type tris-(2,3-epoxypropyl)-isocyanurate crystal according to any one of the first aspect to the third aspect, the method comprising: (i) separating β-type tris-(2,3-epoxypropyl)-isocyanurate contained in a tris-(2,3-epoxypropyl)-isocyanurate solution from the solution as a solid to obtain a crystal or a solution with an increased content ratio of α-type tris-(2,3-epoxypropyl)-isocyanurate; and (ii) extracting 1-type tris-(2,3-epoxypropyl)-isocyanurate contained in the crystal or the solution obtained in (i) with a solvent to obtain a crystal with an increased content ratio of α-type tris-(2,3-epoxypropyl)-isocyanurate;

as a sixth aspect, the method for producing according to the fifth aspect, in which the extraction in (ii) is carried out by using a heated solvent, a solvent at normal temperature, or a cooled solvent;

as a seventh aspect, the method for producing according to any one of the fourth aspect to the sixth aspect, in which the solvent for the tris-(2,3-epoxypropyl)-isocyanurate solution used in (i) is methyl ethyl ketone, acetone, acetonitrile, ethyl acetate, or epichlorohydrin;

as an eighth aspect, the method for producing according to any one of the fifth aspect to the seventh aspect, in which the solvent for extracting β-type tris-(2,3-epoxypropyl)-isocyanurate in (ii) is methyl ethyl ketone, acetone, methanol, ethanol, water, or isopropanol;

as a ninth aspect, a method for producing the α-type tris-(2,3-epoxypropyl)-isocyanurate crystal according to any one of the first aspect to the third aspect, the method comprising (A), (B), and (i'):

(A) generating an epichlorohydrin adduct of cyanuric acid by reacting 1 mol of cyanuric acid with 5 mol to 180 mol of epichlorohydrin and subsequently carrying out dehydrochlorination to obtain a reaction solution containing tris-(2,3-epoxypropyl)-isocyanurate;

(B) adjusting a solid content concentration of the reaction solution containing tris-(2,3-epoxypropyl)-isocyanurate obtained in (A) to 10% by mass to 50% by mass; and (i') separating β-type tris-(2,3-epoxypropyl)-isocyanurate contained in the tris-(2,3-epoxypropyl)-isocyanurate solution obtained in (B) from the solution as a solid to obtain a crystal with an increased content ratio of α-type tris-(2,3-epoxypropyl)-isocyanurate;

as a tenth aspect, a method for producing the α-type tris-(2,3-epoxypropyl)-isocyanurate crystal according to any one of the first aspect to the third aspect, the method comprising (A), (B), (i'), and (ii'):

(A) generating an epichlorohydrin adduct of cyanuric acid by reacting 1 mol of cyanuric acid with 5 mol to 180 mol of epichlorohydrin and subsequently carrying out dehydrochlorination to obtain a reaction solution containing tris-(2,3-epoxypropyl)-isocyanurate;

(B) adjusting a solid content concentration of the reaction solution containing tris-(2,3-epoxypropyl)-isocyanurate obtained in (A) to 10% by mass to 50% by mass;

(i') separating β-type tris-(2,3-epoxypropyl)-isocyanurate contained in the tris-(2,3-epoxypropyl)-isocyanurate solution obtained in (B) from the solution as a solid to obtain a crystal or a solution with an increased content ratio of α-type tris-(2,3-epoxypropyl)-isocyanurate; and (ii') extracting β-type tris-(2,3-epoxypropyl)-isocyanurate contained in the crystal or the solution obtained in (i') with a solvent to obtain a crystal with an increased content ratio of α-type tris-(2,3-epoxypropyl)-isocyanurate;

as an eleventh aspect, the method for producing according to the tenth aspect, in which the extraction in (ii') is carried out by using a heated solvent, a solvent at normal temperature, or a cooled solvent;

as a twelfth aspect, the method for producing according to any one of the ninth aspect to the eleventh aspect, in which the solvent for the tris-(2,3-epoxypropyl)-isocyanurate solution used in (i') is epichlorohydrin;

as a thirteenth aspect, the method for producing according to any one of the tenth aspect to the twelfth aspect, in which the solvent for extracting β-type tris-(2,3-epoxypropyl)-isocyanurate in (ii') is methyl ethyl ketone, acetone, methanol, ethanol, water, or isopropanol;

as a fourteenth aspect, a curable composition comprising the α-type tris-(2,3-epoxypropyl)-isocyanurate crystal according to any one of the first aspect to the third aspect and a carboxylic acid anhydride in a ratio of 0.5 molar equivalent to 1.5 molar equivalent relative to 1 molar equivalent of the crystal;

as a fifteenth aspect, a liquid curable composition comprising the α-type tris-(2,3-epoxypropyl)-isocyanurate crystal according to any one of the first aspect to the third aspect and a liquid carboxylic acid anhydride in a ratio of 0.5 molar equivalent to 1.5 molar equivalent relative to 1 molar equivalent of the crystal;

as a sixteenth aspect, a curable composition comprising the α-type tris-(2,3-epoxypropyl)-isocyanurate crystal according to any one of the first aspect to the third aspect and a cationic curable compound in a ratio of 0.2 molar equivalent to 5 molar equivalent relative to 1 molar equivalent of the crystal;

as a seventeenth aspect, a liquid curable composition comprising the α-type tris-(2,3-epoxypropyl)-isocyanurate crystal according to any one of the first aspect to the third aspect and a liquid cationic curable compound in a ratio of 0.2 molar equivalent to 5 molar equivalent relative to 1 molar equivalent of the crystal;

as an eighteenth aspect, a cured product formed by attaching the curable composition according to any one of the fourteenth aspect to the seventeenth aspect to a substrate and curing the curable composition by heating or light irradiation; and as a nineteenth aspect, the cured product according to the eighteenth aspect, in which the attaching to the substrate is carried out by application, filling, adhesion, or impregnation.

Effects of the Invention

TEPIC (registered trademark, manufactured by NISSAN CHEMICAL INDUSTRIES, LTD.) that is obtained by a usual synthesis method is obtained as a mixture of α-type tris-(2,3-epoxypropyl)-isocyanurate and β-type tris-(2,3-epoxypropyl)-isocyanurate, in theory, in a ratio of 75% by mole and 25% by mole, respectively.

β-type tris-(2,3-epoxypropyl)-isocyanurate generally has low solubility to an organic solvent and β-type tris-(2,3-epoxypropyl)-isocyanurate may be precipitated during long term storage.

By contrast, in the present invention, a solution in which α-type tris-(2,3-epoxypropyl)-isocyanurate crystal, which is stable in a solution state, is dissolved can be obtained by solid-liquid separation of 3-type tris-(2,3-epoxypropyl)-isocyanurate, which is highly crystallized, from the solution state of tris-(2,3-epoxypropyl)-isocyanurate.

As a further stabilization method according to the present invention, the α-type tris-(2,3-epoxypropyl)-isocyanurate crystal obtained by the above method contains l-type tris-(2,3-epoxypropyl)-isocyanurate on the surface and in the inside of the crystal. However, the existing amount of l-type tris-(2,3-epoxypropyl)-isocyanurate near the surface of the crystal, which relates to solubility to the solvent, is reduced by extracting l-type tris-(2,3-epoxypropyl)-isocyanurate mainly from near the surface of the α-type tris-(2,3-epoxypropyl)-isocyanurate crystal with the solvent. Thus, the α-type tris-(2,3-epoxypropyl)-isocyanurate crystal, which has significantly high solubility, can be obtained by this stabilization method.

Thus obtained α-type tris-(2,3-epoxypropyl)-isocyanurate crystal contains β-type tris-(2,3-epoxypropyl)-isocyanurate in the inside of the crystal in a ratio of 2% by mass to 15% by mass, 2% by mass to 10% by mass, 3% by mass to 15% by mass, 3% by mass to 10% by mass, or 4% by mass to 10% by mass.

By using the α-type tris-(2,3-epoxypropyl)-isocyanurate crystal of the present invention, a composition that is homogeneous and can be stored for a long period can be obtained. In addition, the crystal is easily dissolved into solvents and various curing agents. The crystal has excellent compatibility to amines, phenol-based substances, acid anhydrides, carboxylic acids, mercaptans, isocyanates, and polyvalent functional compounds and polyvalent functional macromolecules thereof, which have been known as general epoxy curing agents, and thus a curable composition containing the crystal and the curing agent provides a cured products having excellent homogeneity when the curable composition is cured with the curing agent.

In addition, the cured product has excellent transparency, heat resistance, and light resistance.

MODES FOR CARRYING OUT THE INVENTION

The present invention provides an α-type tris-(2,3-epoxypropyl)-isocyanurate crystal containing β-type tris-(2,3-epoxypropyl)-isocyanurate in the crystal in a ratio of 2% by mass to 15% by mass.

Specifically, the present invention provides the α-type tris-(2,3-epoxypropyl)-isocyanurate crystal in which the ratio of contained β-type tris-(2,3-epoxypropyl)-isocyanurate is in a range of 2% by mass to 15% by mass, 2% by mass to 10% by mass, 3% by mass to 15% by mass, 3% by mass to 10% by mass, or 4% by mass to 10% by mass. In other words, the content ratio of α-type tris-(2,3-epoxypropyl)-isocyanurate in the crystal is 98% by mass to 85% by mass, 98% by mass to 90% by mass, 97% by mass to 85% by mass, 97% by mass to 90% by mass, or 96% by mass to 90% by mass.

The crystal is the α-type tris-(2,3-epoxypropyl)-isocyanurate crystal having a particle diameter of 1 μm to 500 μm or 1 μm to 100 μm.

β-type tris-(2,3-epoxypropyl)-isocyanurate is a crystal having a high melting point of about 150° C. and significantly low solubility and thus the content thereof is preferably 15% by weight or less. A content of more than 15% by weight is not preferable because the solubility of the crystal into solvents becomes significantly low. On the other hand, excessively low content of β-type tris-(2,3-epoxypropyl)-isocyanurate results in high melting point and low solubility. This is because crystallization property is improved due to increase in the purity of α-form and thus the degree of crystallinity is increased. This causes reduction in dissolution rate and results in low solubility. The content of β-type tris-(2,3-epoxypropyl)-isocyanurate in the α-type tris-(2,3-epoxypropyl)-isocyanurate crystal of the present invention is preferably in a ratio of 2% by weight to 15% by weight, preferably 2% by mass to 10% by mass, and preferably 3% by mass to 10% by mass. From the viewpoint of satisfying both preferable melting point and high solubility in use, the preferable range is 4% by mass to 10% by mass, 4% by mass to 8% by mass, 2% by mass to 10% by mass, or 2% by mass to 8% by mass.

The method for producing the crystal of the present invention includes (i) separating l-type tris-(2,3-epoxypropyl)-isocyanurate contained in a tris-(2,3-epoxypropyl)-isocyanurate solution from the solution as a solid to obtain a crystal with an increased content ratio of α-type tris-(2,3-epoxypropyl)-isocyanurate.

In the method for producing the α-type tris-(2,3-epoxypropyl)-isocyanurate crystal of the present invention, the crystal is obtained by separating l-type tris-(2,3-epoxypropyl)-isocyanurate, which is usually contained in tris-(2,3-epoxypropyl)-isocyanurate in a ratio of 25% by mass, as an insoluble component in the solvent. In other words, the crystal is obtained by a method of dissolving α-type tris-(2,3-epoxypropyl)-isocyanurate into a solvent, removing undissolved l-type tris-(2,3-epoxypropyl)-isocyanurate by filtration, and removing the solvent from this solution.

The solvent used in this method is not limited. A solvent having higher solubility to α-type tris-(2,3-epoxypropyl)-isocyanurate and lower solubility to β-type tris-(2,3-epoxypropyl)-isocyanurate, that is, a solvent having large solubility difference between them is preferable.

Examples of the solvent may include methyl ethyl ketone, acetone, acetonitrile, ethyl acetate, and epichlorohydrin.

Subsequently to (i), the method for producing the crystal includes (ii) extracting β-type tris-(2,3-epoxypropyl)-isocyanurate contained in the crystal or the solution of the α-type tris-(2,3-epoxypropyl)-isocyanurate obtained in (i) with a solvent to obtain a crystal with an increased content ratio of α-type tris-(2,3-epoxypropyl)-isocyanurate.

The extraction in (ii) can be carried out by using a heated solvent, a solvent at normal temperature, or a cooled solvent. The heating temperature of the solvent is from a temperature of 10° C. or more higher than room temperature or normal temperature (20° C.) to a temperature equal to or lower than the boiling point of the solvent used at normal pressure. The temperature is preferably a temperature close to the boiling point of the solvent used at normal pressure. The cooled solvent can be used from a temperature 10° C. or more lower than room temperature or normal temperature (20° C.) to a temperature of about −100° C.

β-type tris-(2,3-epoxypropyl)-isocyanurate is extracted from the α-type tris-(2,3-epoxypropyl)-isocyanurate crystal containing 15% by mass or less of β-type tris-(2,3-epoxypropyl)-isocyanurate obtained by the above method with the solvent and thus a crystal having even higher content ratio of α-type tris-(2,3-epoxypropyl)-isocyanurate can be produced. In other words, in this method, the content ratio of α-type tris-(2,3-epoxypropyl)-isocyanurate can be increased by extracting to remove β-type tris-(2,3-epoxypropyl)-isocyanurate using the solvent having smaller solubility difference between α-type tris-(2,3-epoxypropyl)-isocyanurate and β-type tris-(2,3-epoxypropyl)-isocyanurate.

For example, fractional crystallization of β-type is carried out by using the solvent such as acetone that has a larger solubility difference of α-type and β-type of about 20:1 and then the filtrate was concentrated to obtain a crystal having a weight ratio of α-type tris-(2,3-epoxypropyl)-isocyanurate and β-type tris-(2,3-epoxypropyl)-isocyanurate of 94:6. Thereafter, solvent extraction from the crystal with a solvent having a smaller solubility difference of α-type and β-type of about 10:1, such as methyl ethyl ketone, acetone, methanol, ethanol, water, and isopropanol, particularly heated methanol and heated acetone, is carried out to obtain α-type tris-(2,3-epoxypropyl)-isocyanurate having a weight ratio of α-type tris-(2,3-epoxypropyl)-isocyanurate and β-type tris-(2,3-epoxypropyl)-isocyanurate of 96:4.

The α-type tris-(2,3-epoxypropyl)-isocyanurate crystal can be obtained by combining the above methods at the same time.

For example, the crystal can be obtained by once extracting α-type tris-(2,3-epoxypropyl)-isocyanurate with a solvent, thereafter removing 1-type tris-(2,3-epoxypropyl)-isocyanurate by filtration, concentrating the solvent of the filtrate to precipitate α-type tris-(2,3-epoxypropyl)-isocyanurate, and thereafter filtering the precipitated crystal. In this case, the α-type tris-(2,3-epoxypropyl)-isocyanurate crystal containing 1-type tris-(2,3-epoxypropyl)-isocyanurate in a ratio of 2% by weight to 15% by weight can be more effectively obtained by using solubility difference of α-type tris-(2,3-epoxypropyl)-isocyanurate and 1-type tris-(2,3-epoxypropyl)-isocyanurate at each temperature.

In the present invention, α-type tris-(2,3-epoxypropyl)-isocyanurate crystal having high purity can be finally produced through the steps for producing tris-(2,3-epoxypropyl)-isocyanurate.

Namely, the method includes the following (A), (B), and (i'):

(A): generating an epichlorohydrin adduct of cyanuric acid by reacting 1 mol of cyanuric acid with 5 mol to 180 mol of epichlorohydrin and subsequently carrying out dehydrochlorination to obtain a reaction solution containing tris-(2,3-epoxypropyl)-isocyanurate;

(B): adjusting a solid content concentration of the reaction solution containing tris-(2,3-epoxypropyl)-isocyanurate obtained in (A) to 10% by mass to 50% by mass; and (i'): separating β-type tris-(2,3-epoxypropyl)-isocyanurate contained in the tris-(2,3-epoxypropyl)-isocyanurate solution obtained in (B) from the solution as a solid to obtain the crystal with an increased content ratio of α-type tris-(2,3-epoxypropyl)-isocyanurate.

In addition, subsequently to (i'), the method includes the following (ii'):

(ii'): extracting β-type tris-(2,3-epoxypropyl)-isocyanurate from the crystal or the solution of α-type tris-(2,3-epoxypropyl)-isocyanurate obtained in the (i') with a solvent to obtain a crystal with an increased content ratio of α-type tris-(2,3-epoxypropyl)-isocyanurate.

The extraction in (ii') can be carried out by using a heated solvent, a solvent at normal temperature, or a cooled solvent.

The heating temperature of the solvent is from a temperature of 10° C. or more higher than room temperature or normal temperature (20° C.) to a temperature equal to or lower than the boiling point of the solvent used at normal pressure. The temperature is preferably a temperature close to the boiling point of the solvent used at normal pressure. The cooled solvent can be used from a temperature 10° C. or more lower than room temperature or normal temperature (20° C.) to a temperature of about −100° C.

Epichlorohydrin or the like is used as the solvent used in (i').

Methyl ethyl ketone, acetone, methanol, ethanol, water, isopropanol, or the like is used as the solvent used in (ii').

As described above, the α-type tris-(2,3-epoxypropyl)-isocyanurate crystal of the present invention is easily dissolved into solvents and various types of curing agents. The crystal has excellent compatibility to amines, phenol-based substances, acid anhydrides, carboxylic acids, mercaptans, isocyanates, and polyvalent functional compounds and polyvalent functional macromolecules thereof, which have been known as general epoxy curing agents, and thus the crystal provides a cured products having excellent homogeneity when the crystal is cured with the curing agent.

For a powder paint, for example, the crystal provides a homogeneous paint because the crystal has an excellent mixing property when the crystal is melted and kneaded with a polyester having carboxylic acid terminals and thus the paint provides a coating film having excellent flatness. As another example, the crystal provides a composition having excellent homogeneity when the crystal is mixed with an amine-based curing agent. Using slow crystallization rate of this compound, a transparent film made of tris-(2,3-epoxypropyl)-isocyanurate alone also can be obtained by once dissolving the composition into a solvent along with a initiator such as an acid generator, applying the resultant solution onto a substrate and thereafter removing the solvent, and curing the applied film before crystallization.

Use of the α-type tris-(2,3-epoxypropyl)-isocyanurate crystal of the present invention will be described in detail.

First, a curable composition containing the α-type tris-(2,3-epoxypropyl)-isocyanurate crystal and a carboxylic acid anhydride in a ratio of 0.5 molar equivalent to 1.5 molar equivalent and preferably 0.7 molar equivalent to 1.2 molar equivalent relative to 1 molar equivalent of the crystal is prepared, whereby a transparent cured product can be obtained by attaching the curable composition onto a substrate.

Here, examples of the attachment to the substrate may include operations such as application, filling, adhesion, and impregnation.

Examples of the carboxylic acid anhydride may include phthalic anhydride, maleic anhydride, trimellitic anhydride, pyromellitic anhydride, hexahydrophthalic anhydride, 3-methyl-cyclohexane dicarboxylic acid anhydride, 4-methyl-cyclohexane dicarboxylic acid anhydride, a mixture of 3-methyl-cyclohexane dicarboxylic acid anhydride and 4-methyl-cyclohexane dicarboxylic acid anhydride, tetrahydrophthalic anhydride, nadic anhydride, methylnadic anhydride, norbornane-2,3-dicarboxylic acid anhydride, and methylnorbornane-2,3-dicarboxylic acid anhydride.

The α-type tris-(2,3-epoxypropyl)-isocyanurate crystal and the carboxylic acid anhydride can be used as a liquid curable composition with a solid content concentration of 1% by mass to 99% by mass by dissolving them in a solvent. Here, the solid content means a ratio of remaining components after removing the solvents from the solution.

Any commercially available solvents can be used as the solvent. Examples of the solvent may include alcohols such as methanol, ethanol, n-propyl alcohol, isopropyl alcohol, n-butyl alcohol, isobutyl alcohol, t-butyl alcohol, ethylene glycol, and propylene glycol; aromatic hydrocarbons such as benzene, toluene, o-xylene, m-xylene, p-xylene, and mesitylene; aliphatic hydrocarbons such as pentane, hexane, heptane, nonane, and decane; nitriles such as acetonitrile, benzonitrile, acrylonitrile, and adiponitrile; halogenated hydrocarbons such as chlorobenzene, dichlorobenzene, carbon tetrachloride, chloroform, and dichloromethane; ethers such as dibutyl ether, dioxane, diethylene glycol dimethyl ether, triethylene glycol dimethyl ether, tetrahydrofuran, and cyclopentyl methyl ether; ketones such as acetone, methyl ethyl ketone, and methyl isobutyl ketone; esters such as methyl acetate, ethyl acetate, methyl propionate, ethylene glycol monoethyl ether acetate, and diethylene glycol monoethyl ether acetate; epoxies such as epichlorohydrin and CELLOXIDE (trade name, manufactured by Daicel Corporation); amido compounds such as dimethylformamide, N-methylpyrrolidone, N-methylsuccinimide, and N,N-dimethylacetamide; 1,3-dimethyl-2-imidazolidinone, and dimethyl sulfoxide.

As a method for particularly utilizing characteristics of the present invention, a transparent and homogeneous liquid composition can be obtained, even when the solvent is not used, by mixing the α-type tris-(2,3-epoxypropyl)-isocyanurate crystal of the present invention with an acid anhydride such as a carboxylic acid anhydride that is transparent and a liquid state at room temperature and an significantly highly transparent cured product can be obtained by curing the liquid composition. More specifically, a liquid curable composition containing the α-type tris-(2,3-epoxypropyl)-isocyanurate crystal and the liquid carboxylic acid anhydride in a ratio of 0.5 molar equivalent to 1.5 molar equivalent and preferably 0.7 molar equivalent to 1.2 molar equivalent relative to 1 molar equivalent of the crystal is prepared and the liquid curable composition is attached to a substrate, whereby a transparent cured product can be obtained.

Examples of the liquid carboxylic acid anhydride at room temperature may include 3-methyl-cyclohexane dicarboxylic acid anhydride, 4-methyl-cyclohexane dicarboxylic acid anhydride, and a mixture of 3-methyl-cyclohexane dicarboxylic acid anhydride and 4-methyl-cyclohexane dicarboxylic acid anhydride.

A curable composition containing the α-type tris-(2,3-epoxypropyl)-isocyanurate crystal of the present invention and a cationic curable compound in a ratio of 0.2 molar equivalent to 5 molar equivalent relative to 1 molar equivalent of the crystal is prepared and the curable composition is applied to a substrate, whereby a transparent cured product can be obtained. The curable composition can contain the solvent described above.

Examples of the cationic curable compound may include 3,4-epoxycyclohexyl, oxetanyl, and oxetanylene. Available examples of the oxetanyl compound may include OXT series (trade name) from TOAGOSEI CO., LTD. and ETERNACOLL (trade name) from UBE INDUSTRIES, LTD.

As a method for further exploiting characteristics of the present invention, similar to the liquid carboxylic acid anhydride described above, a transparent and homogeneous liquid composition can be obtained by using a cationic curable compound that is transparent and a liquid state at room temperature even when the solvent is not used. A highly transparent cured product can be obtained by curing the liquid composition. For example, a liquid curable composition containing the α-type tris-(2,3-epoxypropyl)-isocyanurate crystal and the liquid cationic curable compound in a ratio of 0.2 molar equivalent to 5 molar equivalent relative to 1 molar equivalent of the crystal is prepared and the liquid curable composition is attached to a substrate, whereby a transparent cured product can be obtained.

An addition amount of less than 0.2 mol is not preferable because the addition of this amount causes difficulty in obtaining a homogeneous liquid composition and results in high viscosity. An addition amount of more than 5 mol is not preferable because the addition of this amount impairs the characteristics of α-type tris-(2,3-epoxypropyl)-isocyanurate such as heat resistance.

As the liquid cationic curable compound, for example, hydrogenated bisphenol A diglycidyl ether; CELLOXIDE, EHPE, and EPOLEAD (trade names) manufactured by Daicel Chemical Co., Ltd. are known. Preferable examples of the liquid cationic curable compound may include TEPIC-VL and TEPIC-PAS (trade names) manufactured by NISSAN CHEMICAL INDUSTRIES, LTD. By using these liquid cationic curable compounds, a cured product that has excellent transparency can be obtained without impairing heat resistance.

Light irradiation or heating to these cationic polymerizable compositions with 0.1% by mass to 5% by mass of a cationic initiator activated by heat or light allows a transparent cured product such as a coating film, an adhesive, and a molded product to be prepared. The cationic initiator activated by heat or light is also called a thermal acid generator or a photoacid generator. Any substance can be used as the cationic initiator as long as an acid, which is a cation source, is generated from the substance by energy such as heat or light.

The photoacid generator or the thermal acid generator is not particularly limited as long as the substance directly or indirectly generates an acid by light irradiation or heating.

Specific usable examples of the photoacid generator may include triazine compounds, acetophenone derivative compounds, disulfonic compounds, diazomethane compounds, sulfonic acid derivative compounds, onium salts such as iodonium salts, sulfonium salts, phosphonium salts, and selenium salts, metallocene complexes, and iron arene complexes.

Examples of the onium salts used as the photoacid generator may include iodonium salts such as diphenyliodonium chloride, diphenyliodonium trifluoromethanesulfonate, diphenyliodonium mesylate, diphenyliodonium tosylate, diphenyliodonium bromide, diphenyliodonium tetrafluoroborate, diphenyliodonium hexafluoroantimonate, diphenyliodonium hexafluoroarsenate, bis(p-tert-butylphenyl)iodonium hexafluorophosphate, bis(p-tert-butylphenyl) iodonium mesylate, bis(p-tert-butylphenyl)iodonium tosylate, bis(p-tert-butylphenyl)iodonium trifluoromethanesulfonate, bis(p-tert-butylphenyl)iodonium tetrafluoroborate, bis(p-tert-butylphenyl)iodonium chloride, bis(p-chlorophenyl)iodonium chloride, and bis(p-chlorophenyl)iodonium tetrafluoroborate; and further, bis(alkylphenyl) iodonium salts such as bis(4-t-butylphenyl)iodonium hexafluorophosphate, alkoxycarbonylalkoxytrialkylaryliodonium salts (such as 4-[(1-ethoxycarbonylethoxy)phenyl]-(2,4,6-trimethylphenyl)-iodonium hexafluorophosphate), and bis(alkoxyaryl)iodonium salts (for example, bis(alkoxyphenyl)iodonium salts such as (4-methoxyphenyl)iodonium hexafluoroantimonate).

Examples of the sulfonium salts may include triphenylsulfonium salts such as triphenylsulfonium chloride, triphenylsulfonium bromide, tri(p-methoxyphenyl)sulfonium tetrafluoroborate, tri(p-methoxyphenyl)sulfonium hexafluorophosphonate, tri(p-ethoxyphenyl)sulfonium tetrafluoroborate, triphenylsulfonium triflate, triphenylsulfonium hexafluoroantimonate, and triphenylsulfonium hexafluorophosphate; and sulfonium salts such as (4-phenylthiophenyl)diphenylsulfonium hexafluoroantimonate, (4-phenylthiophenyl) diphenylsulfonium hexafluorophosphate, bis[4-(diphenylsulfonio)phenyl]sulfide-bis-hexafluoroantimonate, bis[4-(diphenylsulfonio)phenyl]sulfide-bishexafluorophosphate, and (4-methoxyphenyl) diphenylsulfonium hexafluoroantimonate.

Examples of the phosphonium salts may include phosphonium salts such as triphenylphosphonium chloride, triphenylphosphonium bromide, tri(p-methoxyphenyl)phosphonium tetrafluoroborate, tri(p-methoxyphenyl) phosphonium hexafluorophosphate, tri(p-ethoxyphenyl) phosphonium tetrafluoroborate, 4-chlorobenzenediazonium hexafluorophosphate, and benzyltriphenylphosphonium hexafluoroantimonate.

Examples of other photoacid generator may include selenium salts such as triphenylselenium hexafluorophosphate and metallocene complexes such as (η5 or η6-isopropylbenzene) (η5-cyclopentadienyl) iron (II) hexafluorophosphate.

The following compounds can also be used as the photoacid generator.

Formula (A-1)

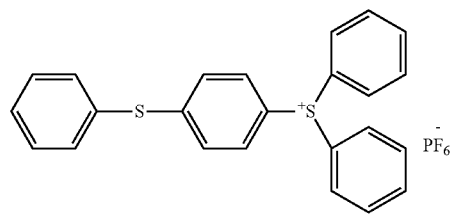

Formula (A-2)

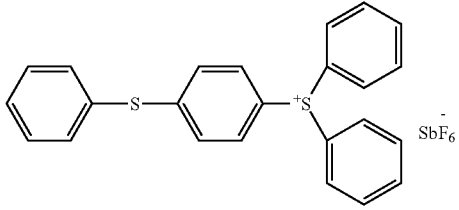

Formula (A-3)

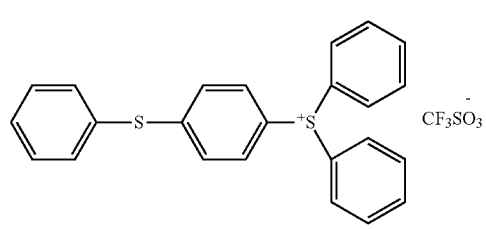

Formula (A-4)

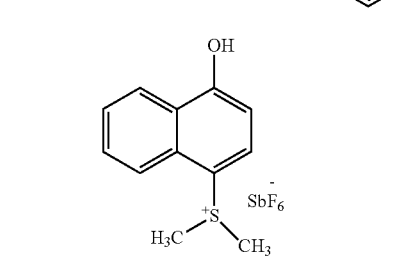

Formula (A-5)

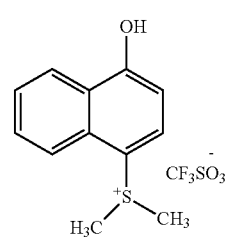

Formula (A-6)

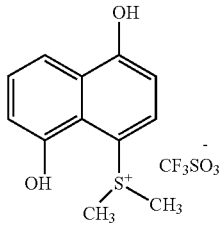

Formula (A-7)

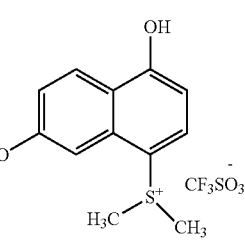

Formula (A-8)

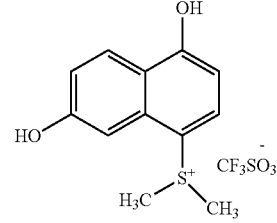

Formula (A-9)

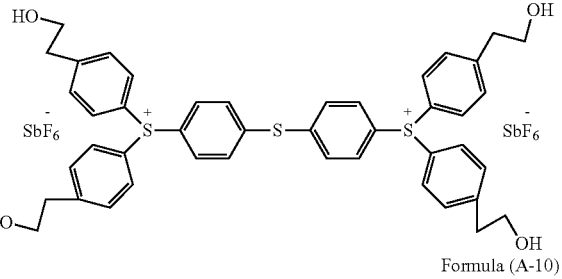

Formula (A-10)

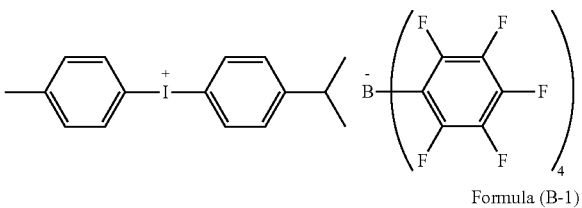

Formula (B-1)

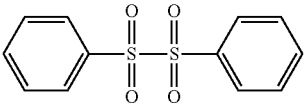

Formula (B-2)

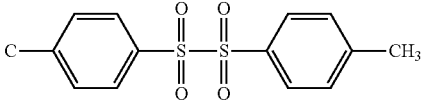

Formula (B-3)

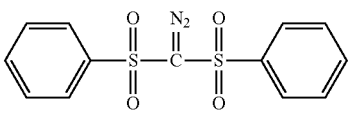

Formula (B-4)

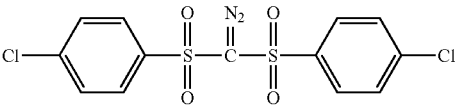

Formula (B-5)
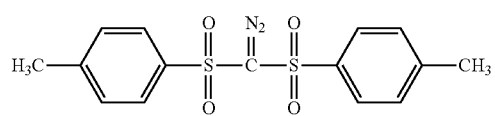
Formula (B-6)
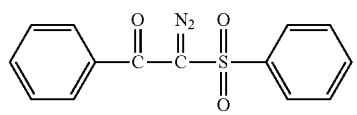
Formula (B-7)
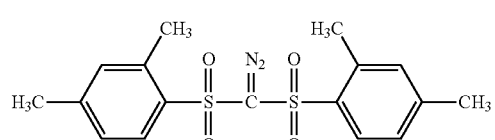
Formula (B-8)
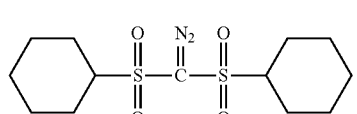
Formula (B-9)
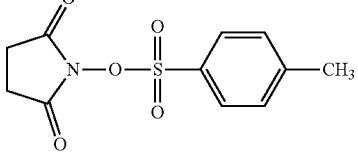
Formula (B-10)
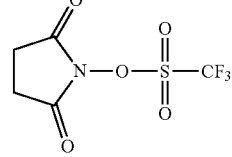
Formula (B-11)
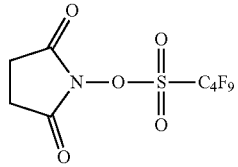
Formula (B-12)
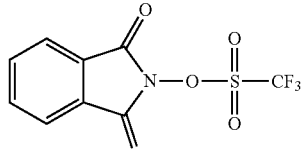
Formula (B-13)
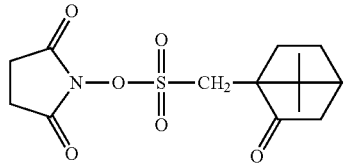
Formula (B-14)
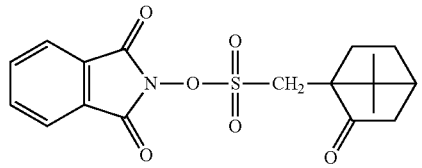
Formula (B-15)
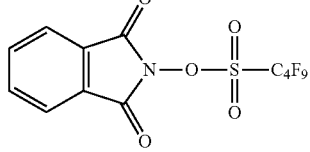
Formula (B-16)
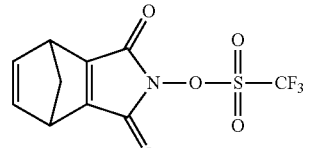
Formula (B-17)
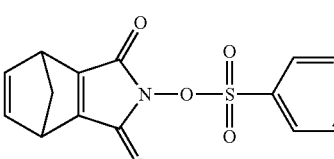
Formula (B-18)
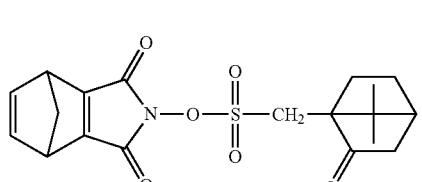
Formula (B-19)
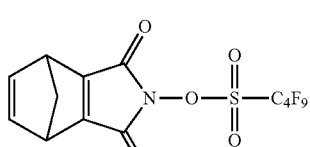
Formula (B-20)
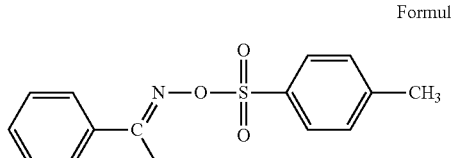
Formula (B-21)
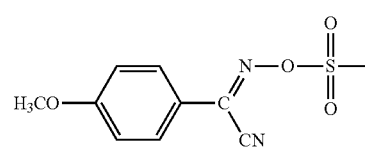
Formula (B-22)
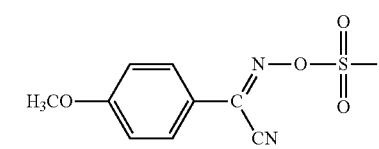

Formula (B-23)
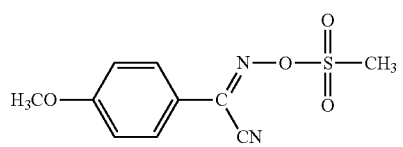
Formula (B-24)
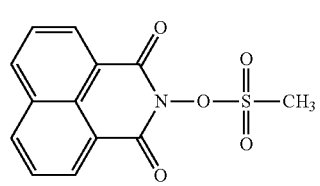
Formula (B-25)
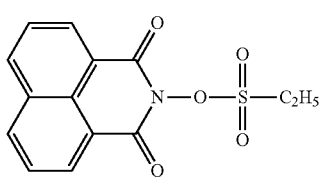
Formula (B-26)
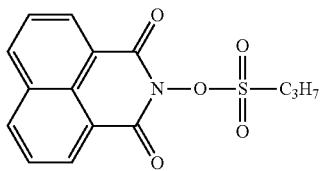
Formula (B-27)
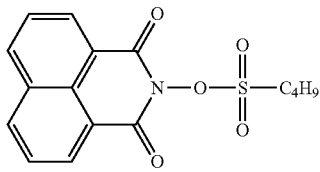
Formula (B-28)
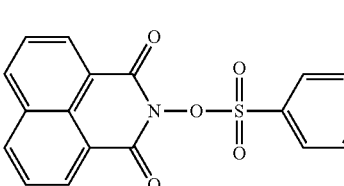
Formula (B-29)
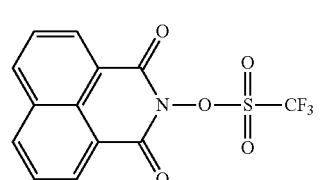
Formula (B-30)
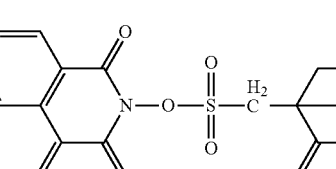
Formula (B-31)
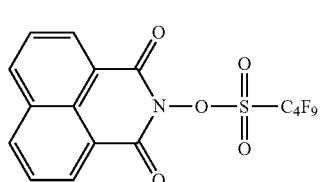
Formula (B-32)
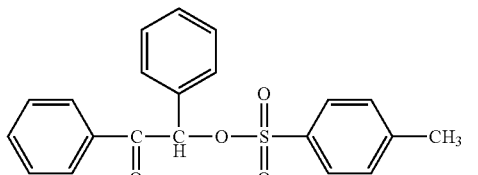
Formula (B-33)
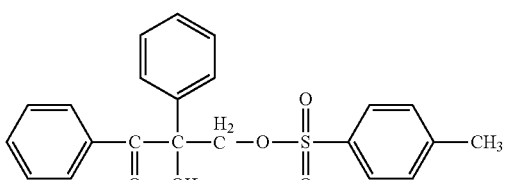
Formula (B-34)
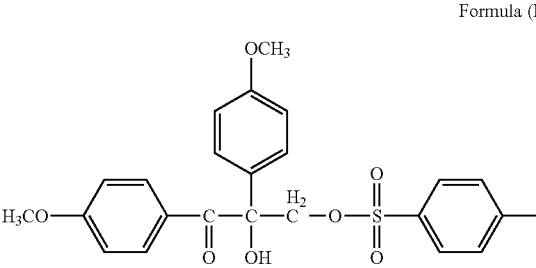
Formula (B-35)
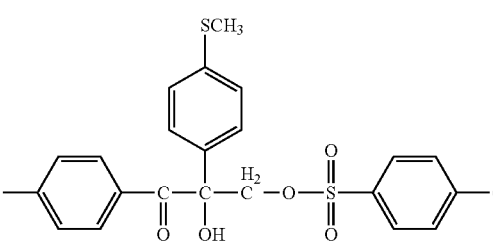
Formula (B-36)
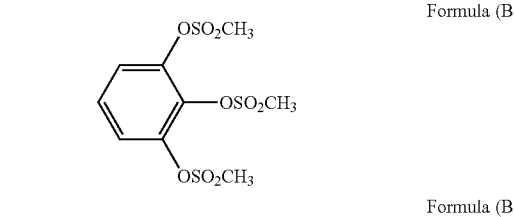
Formula (B-37)
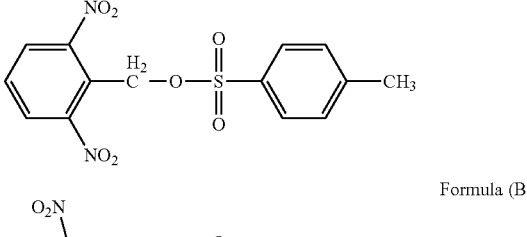
Formula (B-38)
Formula (B-39)
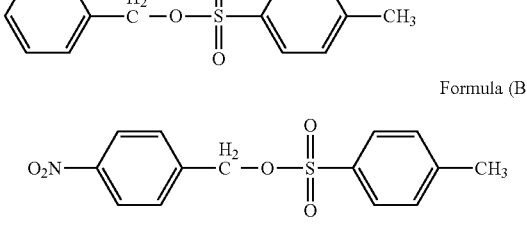

Formula (B-40)

Formula (B-41)

Formula (B-42)

Formula (B-43)

Formula (B-44)

Formula (B-45)

Formula (B-46)

Formula (B-47)

Formula (B-48)

Formula (B-49)

Formula (B-50)

Formula (B-51)

Formula (B-52)

Formula (B-53)

Formula (B-54)

Formula (B-55)

-continued

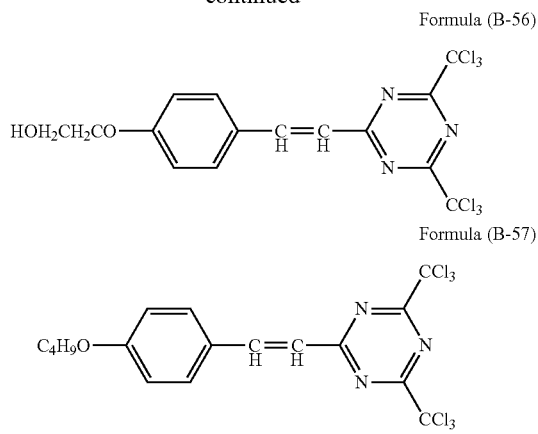

Formula (B-56)

Formula (B-57)

The sulfonium salt compounds and the iodonium salt compounds are preferable for the photoacid generator. Examples of anions of the sulfonium salt compounds and the iodonium salt compounds may include $CF_3SO_3^-$, $C_4F_9SO_3^-$, $C_8F_{17}SO_3^-$, camphor sulfonic acid anion, tosylate anion, $BF_4^-$, $PF_6^-$, $AsF_6^-$, and $SbF_6^-$. In particular, anion species such as phosphorus hexafluoride and antimony hexafluoride, which indicate strong acidity, are preferable.

Examples of the thermal acid generator may include sulfonium salts and phosphonium salts, and the sulfonium salts are preferably used. For example, the following compounds can be exemplified.

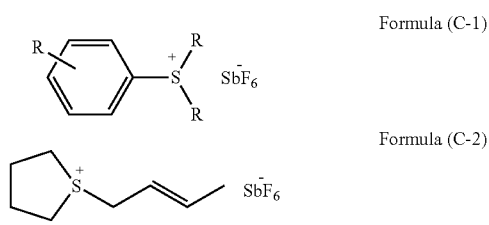

Formula (C-1)

Formula (C-2)

R includes a $C_{1-12}$ alkyl group and a $C_{6-20}$ aryl group, and the $C_{1-12}$ alkyl group is particularly preferable.

These thermal acid generators can be used singly or in combination of two or more of them.

The curable composition of the present invention can provide transparent cured products such as coating films, adhesives, and molded products by adding a curing accelerator, an antioxidant, or other additives, and applying heat.

Depending on the application of the cured product, the thickness of the coating film can be selected in a range from about 0.01 μm to 10 mm. For example, when the coating film is used as a photoresist, the thickness can be about 0.05 μm to 10 μm (particularly, 0.1 μm to 5 μm); when the coating film is used as a printed circuit board, the thickness can be about 10 μm to 5 mm (particularly, 100 μm to 1 mm); and when the coating film is used as an optical thin film, the thickness can be about 0.1 μm to 100 μm (particularly, 0.3 μm to 50 μm).

Examples of irradiation or exposition light when the photoacid generator is used may include gamma rays, X rays, ultraviolet rays, and visible rays. The visible rays or the ultraviolet rays are usually used, and the ultraviolet rays are particularly frequently used. The wavelength of the light is usually about 150 nm to 800 nm, preferably about 150 nm to 600 nm, more preferably about 200 nm to 400 nm, and particularly preferably about 300 nm to 400 nm. The amount of the irradiated light varies depending on the thickness of the coating film. For example, the amount is about 2 mJ/cm² to 20,000 mJ/cm², and preferably about 5 mJ/cm² to 5,000 mJ/cm². The light source can be selected depending on the exposition light. Examples of the usable light source for ultraviolet rays may include a low-pressure mercury lamp, a high pressure mercury lamp, an ultrahigh-pressure mercury lamp, a deuterium lamp, a halogen lamp, laser light (such as helium-cadmium laser and excimer laser). Such light irradiation can promote curing reaction of the composition.

When the thermal acid generator is used or after the light irradiation using the photoacid generator, heating of the coating film is carried out as required, for example, at about 60° C. to 250° C. and preferably at about 100° C. to 200° C. The heating time can be selected in a range of 3 seconds or more (for example about 3 seconds to 5 hours). For example, the heating can be carried out for about 5 seconds to 2 hours and preferably about 20 seconds to 30 minutes, and usually the heating can be carried out for about 1 minute to 3 hours (for example, 5 minutes to 2.5 hours).

Furthermore, when patterns and images are formed (for example, in the case of producing a printed circuit board or the like), pattern exposure of the coating film formed on the substrate may be carried out. The pattern exposure can be carried out by scanning with laser light or light irradiation through a photomask. The patterns or the images can be formed by developing (or dissolving) non-irradiated region (unexposed part) generated by such pattern exposure with a development agent.

An alkaline aqueous solution and an organic solvent can be used as the development liquid.

Examples of the alkaline aqueous solution may include aqueous solutions of alkali metal hydroxides such as potassium hydroxide, sodium hydroxide, potassium carbonate, and sodium carbonate; aqueous solutions of quaternary ammonium hydroxides such as tetramethylammonium hydroxide, tetraethylammonium hydroxide, and choline; and aqueous solutions of amines such as ethanolamine, propylamine, and ethylenediamine.

The alkali development liquid is usually an aqueous solution in a concentration of 10% by mass or less. An aqueous solution in a concentration of 0.1% by mass to 3.0% by mass is preferably used, for example. The development liquid to which alcohols and surfactants are added can be used. Each of them can be contained preferably in a concentration of 0.05 parts by mass to 10 parts by mass relative to 100 parts by mass of the development liquid.

Among them, 0.1% by mass to 2.38% by mass tetramethylammonium hydroxide aqueous solution can be used.

A general organic solvent can be used as the organic solvent for the development liquid. Examples of the organic solvent may include acetone, acetonitrile, toluene, dimethylformamide, methanol, ethanol, isopropanol, propylene glycol methyl ether, propylene glycol ethyl ether, propylene glycol propyl ether, propylene glycol butyl ether, propylene glycol methyl ether acetate, propylene glycol ethyl ether acetate, propylene glycol propyl ether acetate propylene glycol butyl ether acetate, ethyl lactate, and cyclohexanone. These organic solvents can be used singly or in combination of two or more of them. In particular, propylene glycol methyl ether, propylene glycol methyl ether acetate, ethyl lactate, and the like can be preferably used.

Surfactants may be added to the curable composition in order to improve coating properties. Such surfactants are not particularly limited, and examples of the surfactants may include fluorine-containing surfactants, silicone-based surfactants, and nonionic surfactants. These surfactants can be used singly or in combination of two or more of them.

Among these surfactants, the fluorine-containing surfactants are preferable from the viewpoint of high improvement effect for coating properties. Specific examples of the fluorine-containing surfactants may include Eftop EF301, EF303, and EF352 (trade name, manufactured by Tochem Products Co.), Megafac F171, F173, R-30, R-08, R-90, BL-20, and F-482 (trade name, manufactured by Dainippon Ink and Chemicals, Incorporated), Fluorad FC430 and FC431 (trade name, manufactured by Sumitomo 3M Ltd.), and AsahiGuard AG710, and Surflon S-382, SC101, SC102, SC103, SC104, SC105, and SC106 (trade names, manufactured by Asahi Glass Co., Ltd.). The fluorine-containing surfactants, however, are not particularly limited to these products.

The addition amount of the surfactant in the curable composition of the present invention is 0.0008% by mass to 4.5% by mass, preferably 0.0008% by mass to 2.7% by mass, and more preferably 0.0008% by mass to 1.8% by mass in the solid content.

Adhesion accelerators can be added to the curable composition in order to improve adhesion to the substrate after development. Examples of these adhesion accelerators may include chlorosilanes such as trimethylchlorosilane, dimethylvinylchlorosilane, methyldiphenylchlorosilane, and chloromethyldimethylchlorosilane; alkoxysilanes such as trimethylmethoxysilane, dimethyldiethoxysilane, methyldimethoxysilane, dimethylvinylethoxysilane, diphenyldimethoxysilane, and phenyltriethoxysilane; silazanes such as hexamethyldisilazane, N,N'-bis(trimethylsilyl)urea, dimethyltrimethylsilylamine, and trimethylsilylimidazole; silanes such as vinyltrichlorosilane, γ-chloropropyltrimethoxysilane, γ-aminopropyltriethoxysilane, γ-methacryloxypropyltrimethoxysilane, γ-glycidoxypropyltrimethoxysilane, and γ-(N-piperidinyl)propyltrimethoxysilane; heterocyclic compounds such as benzotriazole, benzimidazole, indazole, imidazole, 2-mercaptobenzimidazole, 2-mercaptobenzothiazole, 2-mercaptobenzoxazole, urazole, thiouracil, mercaptoimidazole, and mercaptopyrimidine; urea such as 1,1-dimethylurea and 1,3-dimethylurea; or thiourea compounds. The adhesion accelerators can be used singly or in combination of two or more of them. The addition amount of the adhesion accelerator is usually 18% by mass or less, preferably 0.0008% by mass to 9% by mass, and more preferably 0.04% by mass to 9% by mass in the solid content.

The curable composition of the present invention may contain a sensitizer. Examples of the usable sensitizer may include anthracene, phenothiazine, perylene, thioxanthone, and benzophenonethioxanthone. In addition, examples of sensitizing dyes may include thiopyrylium salt dyes, merocyanine dyes, quinoline dyes, styrylquinoline dyes, ketocoumarin dyes, thioxanthene dyes, xanthene dyes, oxonol dyes, cyanine dyes, rhodamine dyes, and pyrylium salt dyes. The anthracene sensitizers are particularly preferable. Use of the anthracene sensitizers with a cationic curing catalyst (radiation-sensitive cationic polymerization initiator) results in significant improvement of the sensitivity and provides a radical polymerization initiator function. This can simplify the catalyst species in the hybrid type system of the present invention using a cationic curing system and a radical curing system together. Specific examples of the effective anthracene compounds may include dibutoxyanthracene and dipropoxyanthraquinone. The sensitizer is used in an addition amount in a ratio of 0.01% by mass to 20% by mass and preferably 0.01% by mass to 10% by mass in the solid content.

EXAMPLES

Apparatuses used for analyzing samples are as follows.
HPLC
  Apparatus: LC-20A System manufactured by Shimadzu Corporation (analyzing compositions of α-type and β-type)
DSC
  Apparatus: Differential scanning calorimeter DSC1 manufactured by Mettler-Toledo International Inc.
  Temperature rising rate 10° C./min
Melting Point Measuring Equipment
  Apparatus: B-545 manufactured by SIBATA SCIENTIFIC TECHNOLOGY LTD.

<Method for Measuring Ratio of α-Type and β-Type tris-(2,3-epoxypropyl)-isocyanurate>

HPLC measurement was carried out by using a commercially available optical resolution column, CHIRALPAK AS-3 (trade name, manufactured by Daicel Chemical Industries, Ltd. (diameter 0.46 cm×length 10 cm)) and n-hexane/ethanol (60/40 w/w) as an eluent under conditions of a column temperature of 40° C. and a flow rate of 0.4 ml/min. A crystal sample was dissolved in acetonitrile and further diluted with the eluent. The diluted sample was injected into the HPLC apparatus to separate the crystal sample by chromatography. β-type tris-(2,3-epoxypropyl)-isocyanurate was eluted at 11.1 minutes and 13.2 minutes after the injection, whereas α-type tris-(2,3-epoxypropyl)-isocyanurate was eluted at 11.7 minutes and 12.4 minutes after the injection. The ratio of α-type and β-type in the entire crystal was calculated according to the peak area ratio of each type.

<Measurement of Particle Diameter and Particle Size Distribution>

The measurement was carried out by a wet method with a laser diffraction light scattering particle size distribution measuring device using methanol as a dispersion medium. As the average particle diameter, a volume-based median diameter (median diameter) D50 was used. As the values indicating distribution, a diameter at 10% cumulative volume (D10) and a diameter at 90% cumulative volume (D90) were indicated.

Synthesis Example 1

To a reaction flask having a capacity of 2 liters equipped with a stirrer, 30 g of water, 5.5 g of tetramethylammonium chloride, 1,388 g (15 mol) of epichlorohydrin, and 129 g (1 mol) of isocyanuric acid were charged to form a reaction mixture. Subsequently, the reaction mixture in the flask was heated with stirring to raise the temperature. When the temperature of the reaction mixture reached 89° C., the reaction mixture began to boil under atmospheric pressure. The reaction mixture, however, was continued to be heated. For 5 hours, the generated vapor was cooled with a condenser; the total amount of liquefied epichlorohydrin was continuously refluxed into the flask; and liquefied water was continued to be discharged out of the flask. Consequently, the temperature of the reaction mixture reached 120° C. At this time, the heating was stopped and the reaction mixture was cooled to obtain reaction product having a temperature of 45° C. Unreacted cyanuric acid was not detected in the product.

Subsequently, while maintaining the total amount of the reaction product in the flask at 50° C., 256 g (3.2 mol as NaOH) of 50% by mass sodium hydroxide aqueous solution was started to be added dropwise to this reaction product under a reduced pressure of 100 mmHg to from a reaction mixture. In this case, water and epichlorohydrin were simultaneously evaporated from this reaction mixture with vigorous stirring. While gradually increasing the degree of reduction in pressure, the vapor was continuously cooled with the condenser; the total amount of the liquefied epichlorohydrin was continuously refluxed into the flask; and the liquefied water was continuously discharged out of the flask. When the degree of reduction in pressure reached 60 mmHg, the dropwise addition was completed to obtain a slurry containing precipitated sodium chloride. Six hours were required from the start of dropwise addition to this completion. During this period, the reaction mixture with stirring was clouded with precipitates of sodium chloride. The reaction mixture, however, was maintained homogeneously from the beginning to the end. According to the liquid chromatography analysis, the content ratio of the compound having a 2-hydroxy-3-chloropropyl group contained in the slurry was 1% or less.

The obtained tris-(2,3-epoxypropyl)-isocyanurate had (a mass ratio of α-type:β-type=75:25). The particle diameter of the obtained crystal was 1 μm to 100 μm.

Example 1

700 g (2.25 mol) of tris-(2,3-epoxypropyl)-isocyanurate prepared in Synthesis Example 1 and 528 g of acetonitrile were mixed. The temperature of the mixture was raised to 60° C. and the mixture was stirred for 10 minutes. Thereafter, the mixture was cooled to 55° C., and 0.7 g (2.25 mmol) of tris-(2,3-epoxypropyl)-isocyanurate (mass ratio of α-type:β-type=75:25) was added as a seed crystal. The resultant mixture was gradually cooled from 55° C. to 15° C. over 2 hours and stirred for 30 minutes. Thereafter, the crystals were filtered and the obtained crystal was washed with 315 g of methanol twice. This washing liquid was 651 g and was used later.

1,028 g of this filtrate containing α-type in a higher ratio was concentrated to 673 g. 133 g of acetonitrile, 198 g of methanol, and 651 g of washing liquid previously recovered were mixed with this concentrated filtrate and the temperature of the mixture was raised to 60° C. and the subsequent mixture was stirred for 10 minutes. Thereafter, the mixture was gradually cooled, and at 45° C., 18.4 g (59.1 mmol) of tris-(2,3-epoxypropyl)-isocyanurate (mass ratio of α-type:β-type=75:25) was added as a seed crystal. The mixture was cooled to 10° C. over 2 hours and stirred for 2 hours and 30 minutes. Thereafter, the crystal was filtered and washed with 290 g of methanol twice. The obtained crystal was dried under reduced pressure to obtain 480 g (1.54 mol) of tris-(2,3-epoxypropyl)-isocyanurate (mass ratio of α-type:β-type=93:7). The particle diameter of the obtained crystal was 1 μm to 100 μm.

Example 2

30 g (96 mmol) of highly pure tris-(2,3-epoxypropyl)-isocyanurate prepared in Synthesis Example 1 and 200 g of acetone were mixed. The mixture was stirred at 10° C. for 3 hours. Thereafter, the crystal was filtered to obtain a filtrate containing α-type in a higher ratio. After this filtrate was concentrated and dried, 14 g of acetone was added and the mixture was stirred at 55° C. for 1 hour. Thereafter, the mixture was filtered at a high temperature of 55° C. and the obtained crystal was dried under reduced pressure to obtain 6.5 g (21.0 mmol) of tris-(2,3-epoxypropyl)-isocyanurate (mass ratio of α-type:β-type=97:3). The particle diameter of the obtained crystal was 1 μm to 100 μm.

Example 3

7.0 g (22.5 mmol) of tris-(2,3-epoxypropyl)-isocyanurate (mass ratio of α-type:β-type=93:7) obtained in Example 1 and 63 g of methanol were mixed. The temperature of the mixture was raised to 55° C. and the mixture was stirred for 10 minutes. Thereafter, the mixture was filtered at a high temperature of 55° C. and the obtained crystal was dried under reduced pressure to obtain 0.56 g (3.2 mmol) of tris-(2,3-epoxypropyl)-isocyanurate (mass ratio of α-type:β-type=98:2). The particle diameter of the obtained crystal was 1 μm to 100 μm.

(Melting Point Measurement)

The melting point was measured by the method in accordance with JIS-K0064 (Test methods for melting point and melting range of chemical products).

Melting points of tris-(2,3-epoxypropyl)-isocyanurate having different composition ratios of α-type and 1-type were measured with DSC and the melting point measuring equipment. The measured value of DSC is a peak top.

TABLE 1

| Sample | α-type:β-type (% by mass) | DSC (° C.) | Melting point measuring equipment (° C.) |
|---|---|---|---|
| Synthesis Example 1 | 75:25 | 111° C. | 103.1-103.9° C. |
| Example 1 | 93:7 | 112° C. | 105.0-105.3° C. |
| Example 2 | 97:3 | 114° C. | 108.9-109.2° C. |
| Example 3 | 98:2 | 115° C. | 109.4-110.1° C. |

(Solubility Test)

1 g of the sample (tris-(2,3-epoxypropyl)-isocyanurate) that is subjected to solubility test was weighed and the amount of a solvent required to form the homogeneous and clear solution at 25° C. was measured. From this amount of solvent, the mass of each sample that was capable of being dissolved into 100 g of the solvent was calculated. The results are listed in Table 2.

TABLE 2

| Sample | α-type:β-type (% by mass) | Methyl ethyl ketone | Ethyl acetate | Toluene |
|---|---|---|---|---|
| Synthesis Example 1 | 75:25 | 1.7 g | 1.4 g | 0.5 g |
| Example 1 | 93:7 | 6.8 g | 6.3 g | 1.8 g |
| Example 2 | 97:3 | 9.3 g | 6.3 g | 2.1 g |
| Example 3 | 98:2 | 9.0 g | 6.1 g | 2.0 g |

Tris-(2,3-epoxypropyl)-isocyanurate (mass ratio of α-type:β-type=99:1) had a melting point of 117° C. and thus the heating and melting temperature at the time of producing the epoxy composition became high. In addition, as can be seen from the melting point, this tris-(2,3-epoxypropyl)-isocyanurate had significantly high crystallinity and thus the dissolution rate of this tris-(2,3-epoxypropyl)-isocyanurate for dissolution into the solvent was slower than that of tris-(2,3-epoxypropyl)-isocyanurate (mass ratio of α-type:β-type was in a range of 98:2 to 85:15).

Example 4

Into a flask, 10.0 g of the α-type tris-(2,3-epoxypropyl)-isocyanurate crystal obtained in Example 1 and 16.4 g of RIKACID MH-700 (manufactured by New Japan Chemical Co., Ltd., a liquid mixture of 4-methylhexahydrophthalic anhydride and hexahydrophthalic anhydride in a mass ratio of 70/30) were charged and mixed at 100° C. until the mixture became homogeneous. The mixture was once cooled to 80° C. and 100 mg of tetra-n-butylphosphonium-o,o-diethylphosphorodithioate (manufactured by Nippon Chemical Industrial Co., Ltd., trade name HISHICOLIN PX-4ET) was added and dissolved. Thereafter, degassing and removal of volatile content were carried out under reduced pressure for several minutes.

Thereafter, the mixture was casted between mold release agent-treated glass plates between which a spacer having a thickness of 3 mm was sandwiched.

After cooling, the composition was left to stand at room temperature for one week. The composition remained to be a clear and homogeneous composition without precipitating tris-(2,3-epoxypropyl)-isocyanurate.

Example 5

1.90 kg (6.39 mol) of highly pure tris-(2,3-epoxypropyl)-isocyanurate prepared in Synthesis Example 1 and 12.7 kg of acetone were mixed. The mixture was stirred at 10° C. for 2 hours. Thereafter, the crystal was filtered to obtain a filtrate containing α-type in a higher ratio. This filtrate was added to 14.3 kg of methanol and the resultant mixture was stirred at −5° C. Thereafter, the mixture was filtered and the obtained crystal was dried under reduced pressure to obtain 571 g (1.92 mol) of tris-(2,3-epoxypropyl)-isocyanurate (mass ratio of α-type:β-type=97:3).

Example 6

80.0 kg (269 mol) of highly pure tris-(2,3-epoxypropyl)-isocyanurate prepared in Synthesis Example 1 and 680 kg of acetone were mixed. The mixture was stirred at 9° C. Thereafter, the crystal was filtered to obtain a filtrate containing α-type in a higher ratio. After this filtrate was concentrated under reduced pressure at 40° C., 243 kg of methanol was added and the resultant mixture was cooled to 20° C. Thereafter, the mixture was filtered and the obtained crystal was dried under reduced pressure to obtain 37.3 g (125 mol) of tris-(2,3-epoxypropyl)-isocyanurate (mass ratio of α-type:β-type=98:2).

Example 7

12.5 kg (42 mmol) of highly pure tris-(2,3-epoxypropyl)-isocyanurate prepared in Synthesis Example 1 and 106 kg of acetone were mixed. The mixture was stirred at 6° C. Thereafter, the crystal was filtered to obtain a filtrate containing α-type in a higher ratio. After this filtrate was concentrated under reduced pressure at 50° C., 90 kg was added of methanol and the resultant mixture was cooled to −20° C. Thereafter, the mixture was filtered and the obtained crystal was dried under reduced pressure to obtain 9.3 g (31 mmol) of tris-(2,3-epoxypropyl)-isocyanurate (mass ratio of α-type:β-type=94:6).

Example 8

A filtrate containing α-type in a higher ratio was obtained in the same manner as Example 7. After this filtrate was concentrated under reduced pressure at 40° C., 88 kg of ion exchanged water was added and the resultant mixture was cooled to 0° C. Thereafter, the mixture was filtered and the obtained crystal was dried under reduced pressure to obtain 6.1 g (21 mmol) of tris-(2,3-epoxypropyl)-isocyanurate (mass ratio of α-type:β-type=97:3).

Example 9

20.0 g (67 mmol) of highly pure tris-(2,3-epoxypropyl)-isocyanurate prepared in Synthesis Example 1 and 170 g of acetone were mixed. The mixture was stirred at 6° C. Thereafter, the crystal was filtered to obtain a filtrate containing α-type in a higher ratio. The filtrate was concentrated under reduced pressure at 40° C., and thereafter cooled to 20° C. The precipitated crystal was filtered and the obtained crystal was dried under reduced pressure to obtain 13.6 g (46 mmol) of tris-(2,3-epoxypropyl)-isocyanurate (mass ratio of α-type:β-type=94:6).

Example 10

240 g (807 mmol) of highly pure tris-(2,3-epoxypropyl)-isocyanurate prepared in Synthesis Example 1 and 2,040 g of acetone were mixed. The mixture was stirred at 6° C. Thereafter, the crystal was filtered to obtain a filtrate containing α-type in a higher ratio. This filtrate was concentrated under reduced pressure at 40° C. and thereafter dried. The obtained tris-(2,3-epoxypropyl)-isocyanurate (mass ratio of α-type:β-type=95:5) was 198 g (666 mmol).

Example 11

20.0 g (67 mmol) of highly pure tris-(2,3-epoxypropyl)-isocyanurate prepared in Synthesis Example 1 and 170 g of acetone were mixed. The mixture was stirred at 6° C. Thereafter, the crystal was filtered to obtain a filtrate containing α-type in a higher ratio. After the filtrate was concentrated under reduced pressure at 40° C., 65 g of methanol was added. Further concentration of the resultant mixture caused precipitation of the crystal. The mixture was cooled to 20° C. and the crystal was filtered. The obtained crystal was dried under reduced pressure to obtain 13.9 g (47 mmol) of tris-(2,3-epoxypropyl)-isocyanurate (mass ratio of α-type:β-type=94:6).

Example 12

5.0 g (17 mmol) of highly pure tris-(2,3-epoxypropyl)-isocyanurate prepared in Synthesis Example 1 and 42.5 g of epichlorohydrin were mixed. The mixture was stirred at 6° C. Thereafter, the crystal was filtered to obtain a filtrate containing α-type in a higher ratio. This filtrate was concentrated under reduced pressure at 60° C. and thereafter dried. The obtained tris-(2,3-epoxypropyl)-isocyanurate (mass ratio of α-type:β-type=91:9) was 4.0 g (13 mmol).

Example 13

5.0 g (17 mmol) of highly pure tris-(2,3-epoxypropyl)-isocyanurate prepared in Synthesis Example 1 and 42.5 g of epichlorohydrin were mixed. The mixture was stirred at 6° C. Thereafter, the crystal was filtered to obtain a filtrate containing α-type in a higher ratio. To this filtrate, 785 g of methanol was added and the resultant mixture was cooled to −78° C. Thereafter, the mixture was filtered and the obtained crystal was dried under reduced pressure to obtain tris-(2, 3-epoxypropyl)-isocyanurate (mass ratio of α-type:β-type=92:8) was 3.2 g (11 mmol).
(Solubility Test)

4 g of the sample (tris-(2,3-epoxypropyl)-isocyanurate) that is subjected to solubility test was weighed and the amount of solvent required to form the homogeneous and clear solution at 25° C. was measured. From this amount of solvent, the mass of each sample that was capable of being dissolved into 100 g of the solvent was calculated. The results are listed in Table 3. In Table 3, PGME is propylene glycol monomethyl ether and PGMEA is propylene glycol monomethyl ether acetate.

TABLE 3

| Sample | α-type:β-type (% by mass) | Acetone | Acetonitrile | PGME | PGMEA |
|---|---|---|---|---|---|
| Synthesis Example 1 | 75:25 | 7.8 g | 17 g | 1.6 g | 2.2 g |
| Example 10 | 95:5 | 24 g | 71 g | — | — |
| Example 6 | 98:2 | — | — | 2.5 g | 5.1 g |

Comparative Example 1

Into a flask, 10.0 g of highly pure α-type tris-(2,3-epoxypropyl)-isocyanurate (mass ratio of α-type:β-type=75:25) prepared in Synthesis Example 1 and 16.4 g of RIKACID MH-700 (manufactured by New Japan Chemical Co., Ltd., a liquid mixture of 4-methylhexahydrophthalic anhydride and hexahydrophthalic anhydride in a mass ratio of 70/30) were charged and mixed at 100° C. until the mixture became homogeneous. The mixture was once cooled to 80° C., and 100 mg of tetra-n-butylphosphonium-o,o-diethylphosphorodithioate (manufactured by Nippon Chemical Industrial Co., Ltd., trade name HISHICOLIN PX-4ET) was added and dissolved. Thereafter, degassing and removal of volatile matters were carried out under reduced pressure for several minutes.

Thereafter, the mixture was casted between mold release agent-treated glass plates between which a spacer having a thickness of 3 mm was sandwiched.

After cooling, the composition was left to stand for several hours. The precipitate of tris-(2,3-epoxypropyl)-isocyanurate was observed.

Example 14

Into a flask, 10.0 g of the α-type tris-(2,3-epoxypropyl)-isocyanurate crystal obtained in Example 1 and 16.4 g of RIKACID MH-700 (manufactured by New Japan Chemical Co., Ltd., a liquid mixture of 4-methylhexahydrophthalic anhydride and hexahydrophthalic anhydride in a mass ratio of 70/30) were charged and mixed at 100° C. until the mixture became homogeneous. The mixture was once cooled to 80° C., and 100 mg of tetra-n-butylphosphonium-o,o-diethylphosphorodithioate (manufactured by Nippon Chemical Industrial Co., Ltd., trade name HISHICOLIN PX-4ET) was added and dissolved. Thereafter, degassing and removal of volatile matters were carried out under reduced pressure for several minutes.

Thereafter, the mixture was casted between mold release agent-treated glass plates between which a spacer having a thickness of 3 mm was sandwiched.

This mixture was heated at 100° C. for 2 hours. Thereafter, the temperature was raised to 150° C. and the mixture was heated at this temperature for 5 hours to obtain a cured product.

This cured product was evaluated in accordance with "Testing methods for thermosetting plastics" in Japanese Industrial Standards (JIS-K6911).

As the result of the bending test (three specimens were tested), the bending strength was 130 MPa. The flexural modulus was 4.000 MPa. The maximum amount of deflection was 7.7 mm. As the results of thermal analysis (TMA), Tg was 185° C. and the linear expansion coefficient (CTE1) was 73 ppm/° C. The transmittance of the cured product was 90% at 400 nm.

Comparative Example 2

Into a flask, 10.0 g of highly pure tris-(2,3-epoxypropyl)-isocyanurate (mass ratio of α-type:β-type=75:25) obtained in Synthesis Example 1 and 16.4 g of RIKACID MH-700 (manufactured by New Japan Chemical Co., Ltd., a liquid mixture of 4-methylhexahydrophthalic anhydride and hexahydrophthalic anhydride in a mass ratio of 70/30) were charged and mixed at 100° C. until the mixture became homogeneous. The mixture was once cooled to 80° C. and 100 mg of tetra-n-butylphosphonium-o,o-diethylphosphorodithioate (manufactured by Nippon Chemical Industrial Co., Ltd., trade name HISHICOLIN PX-4ET) was added and dissolved. Thereafter, degassing and removal of volatile matters were carried out by reduced pressure for several minutes.

Thereafter, the mixture was casted between mold release agent-treated glass plates between which a spacer having a thickness of 3 mm was sandwiched.

This mixture was heated at 100° C. for 2 hours. Thereafter, the temperature was raised to 150° C. and the mixture was heated at this temperature for 5 hours to obtain a cured product.

This cured product was evaluated in accordance with "Testing methods for thermosetting plastics" in Japanese Industrial Standards (JIS-K6911).

As the result of the bending test (three specimens are tested), the bending strength was 140 MPa. The flexural modulus was 4.100 MPa. The maximum amount of deflection was 7.7 mm. As the results of thermal analysis (TMA), Tg was 183° C. and the linear expansion coefficient (CTE1) was 72 ppm/° C. The transmittance of the cured product was 90% at 400 nm.

INDUSTRIAL APPLICABILITY

According to the present invention, tris-(2,3-epoxypropyl)-isocyanurate crystal having excellent workability including high solubility during use and difficulty in precipitating a crystal during storage can be obtained. The epoxy composition using this crystal can provide a composition that is homogeneous and can be stored for a long period. The cured product of the composition having excellent transparency, high heat resistance, and high light resistance can be obtained when the composition is cured.

The invention claimed is:
1. A method comprising
producing an α-type tris-(2,3-epoxypropyl)-isocyanurate crystal comprising β-type tris-(2,3-epoxypropyl)-isocyanurate in the crystal in a ratio of 2% by mass to 15% by mass and the crystal having a particle diameter of 1 μm to 500 μm, the method comprising:
generating tris-(2,3-epoxypropyl)-isocyanurate as an epichlorohydrin adduct of cyanuric acid by reacting 1 mol of cyanuric acid with 5 mol to 180 mol of epichlorohydrin and subsequently carrying out dehydrochlorination;

forming a tris-(2,3-epoxypropyl)-isocyanurate solution from the generated tris-(2,3-epoxypropyl)-isocyanurate and a solvent that includes one or more of methyl ethyl ketone, acetone, acetonitrile, ethyl acetate, or epichlorohydrin;

separating undissolved β-type tris-(2,3-epoxypropyl)-isocyanurate from the tris-(2,3-epoxypropyl)-isocyanurate solution as a solid to obtain a crystal with an increased content ratio of α-type tris-(2,3-epoxypropyl)-isocyanurate; and extracting β-type tris-(2,3-epoxypropyl)-isocyanurate contained in the crystal or the tris-(2,3-epoxypropyl)-isocyanurate solution with an additional solvent to obtain a crystal with a further increased content ratio of α-type tris-(2,3-epoxypropyl)-isocyanurate, wherein the additional solvent is one or more of methyl ethyl ketone, acetone, methanol, ethanol, water, or isopropanol.

2. The method according to claim 1, wherein the additional solvent in the extracting is a heated solvent.

3. The method according to claim 1, wherein the method further comprises:

following the generating of the tris-(2,3-epoxypropyl)-isocyanurate in a reaction solution, adjusting a solid content concentration of the reaction solution containing the tris-(2,3-epoxypropyl)-isocyanurate to 10% by mass to 50% by mass to form the tris-(2,3-epoxypropyl)-isocyanurate solution.

4. He method according to claim 1, wherein the solvent for forming the tris-(2,3-epoxypropyl)-isocyanurate solution is epichlorohydrin.

5. The method according to claim 1, further comprising mixing the α-type tris-(2,3-epoxypropyl)-isocyanurate crystal comprising β-type tris-(2,3-epoxypropyl)-isocyanurate in the crystal in the ratio of 2% by mass to 15% by mass and the crystal having the particle diameter of 1 μm to 500 μm, and (1) a carboxylic acid anhydride in a ratio of 0.5 molar equivalent to 1.5 molar equivalent relative to 1 molar equivalent of the crystal, or (2) a cationic curable compound in a ratio of 0.2 molar equivalent to 5 molar equivalent relative to 1 molar equivalent of the crystal, to form a curable composition, wherein the curable composition has a solid content concentration of 1% by mass to 99% by mass.

6. The method according to claim 1, wherein the additional solvent in the extracting is a solvent at normal temperature.

7. The method according to claim 1, wherein the additional solvent in the extracting is a cooled solvent.

* * * * *